US010765609B2

(12) United States Patent
Takahashi et al.

(10) Patent No.: US 10,765,609 B2
(45) Date of Patent: Sep. 8, 2020

(54) ORAL COMPOSITION

(71) Applicant: Kao Corporation, Chuo-ku, Tokyo (JP)

(72) Inventors: Noritaka Takahashi, Tokyo (JP);
Ryosuke Nagata, Ichikawa (JP);
Takuya Asada, Yoshikawa (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/305,643

(22) PCT Filed: May 29, 2017

(86) PCT No.: PCT/JP2017/019822
§ 371 (c)(1),
(2) Date: Nov. 29, 2018

(87) PCT Pub. No.: WO2017/209020
PCT Pub. Date: Dec. 7, 2017

(65) Prior Publication Data
US 2019/0358133 A1 Nov. 28, 2019

(30) Foreign Application Priority Data
May 31, 2016 (JP) .................................. 2016-109189

(51) Int. Cl.
*A61K 8/21* (2006.01)
*A61K 8/24* (2006.01)
*A61K 8/26* (2006.01)
*A61K 8/34* (2006.01)
*A61K 8/36* (2006.01)
*A61K 8/49* (2006.01)
*A61K 8/86* (2006.01)
*A61Q 11/00* (2006.01)

(52) U.S. Cl.
CPC .................. *A61K 8/21* (2013.01); *A61K 8/24* (2013.01); *A61K 8/26* (2013.01); *A61K 8/342* (2013.01); *A61K 8/36* (2013.01); *A61K 8/49* (2013.01); *A61K 8/86* (2013.01); *A61Q 11/00* (2013.01); *A61K 2800/28* (2013.01)

(58) Field of Classification Search
CPC ..................................... A61K 8/18; C11D 3/14
USPC ........................................................ 424/49
See application file for complete search history.

(56) References Cited

U.S. PATENT DOCUMENTS

| 2008/0081023 | A1* | 4/2008 | Deckner | ............... | A61K 8/042 424/49 |
|---|---|---|---|---|---|
| 2009/0246151 | A1 | 10/2009 | LeBlanc et al. | | |
| 2013/0108559 | A1 | 5/2013 | Midha et al. | | |
| 2014/0308355 | A1 | 10/2014 | Midha et al. | | |
| 2015/0007399 | A1* | 1/2015 | Gonzales | ................. | A61K 8/25 15/104.93 |

FOREIGN PATENT DOCUMENTS

| JP | S57-093906 | | 6/1982 |
| JP | 2005-289917 | A | 10/2005 |
| JP | 2007-045786 | A | 2/2007 |
| JP | 2009-155217 | A | 7/2009 |
| JP | 2010-260794 | A | 11/2010 |
| JP | 2011-515492 | A | 5/2011 |
| JP | 2014-125443 | A | 7/2014 |
| JP | 6096396 | B | 2/2017 |
| JP | 2017-214319 | A | 12/2017 |
| JP | 2017-214347 | A | 12/2017 |
| WO | WO 2009/120854 | A2 | 10/2009 |
| WO | WO 2014/169082 | A1 | 10/2014 |

OTHER PUBLICATIONS

Colgate, "Fluoride Conversions." www.colgateprofessional.com (Year: 2013).*
International Search Report (ISR) for PCT/JP2017/019822; I.A. fd May 29, 2017, dated Aug. 15, 2017 from the Japan Patent Office, Tokyo, Japan.
Written Opinion of the International Searching Authority for PCT/JP2017/019822; I.A. fd May 29, 2017, dated Aug. 15, 2017, by the Japan Patent Office, Tokyo, Japan.
The extended European search report, including the supplementary European search report and the European search opinion for EP Application No. 17806575.1, dated Nov. 29, 2019, European Patent Office, Munich, Germany.

* cited by examiner

*Primary Examiner* — Walter E Webb
(74) *Attorney, Agent, or Firm* — Sterne, Kessler, Goldstein & Fox P.L.L.C.

(57) ABSTRACT

The present invention is directed to an oral composition having an improved ability to incorporate fluoride ions into tooth enamel and an enhanced remineralization effect.

17 Claims, 1 Drawing Sheet

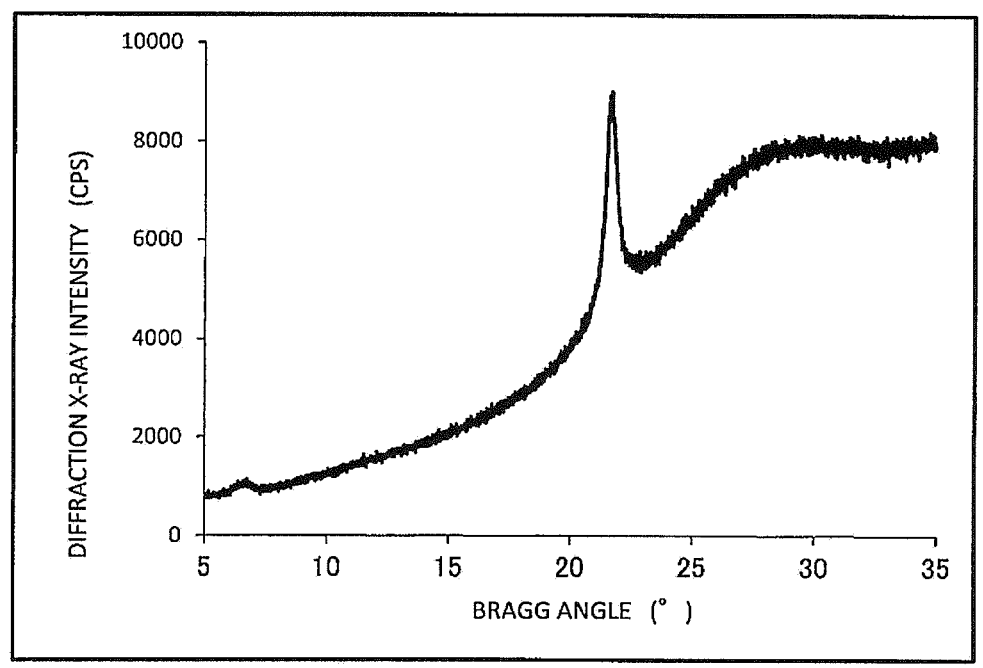

ORAL COMPOSITION

FIELD OF THE INVENTION

The present invention relates to an oral composition.

BACKGROUND OF THE INVENTION

Sparingly water-soluble active ingredients such as glycyrrhetinic acid and tocopherols can impart various pharmacological actions and therefore have been conventionally widely used as medicinal ingredients. For example, Patent Literature 1 discloses a dentifrice composition exhibiting excellent medicinal effects and having enhanced persistence thereof by containing a sparingly water-soluble active ingredient such as tocopherols and an oily ingredient, as well as a sucrose fatty acid ester and an anionic surfactant each at a specific mass ratio. Patent Literature 2 discloses a dentifrice composition containing a specific amount of a specific peppermint oil together with the above-mentioned active ingredient and surfactant so as to express good flavor in addition to the excellent medicinal effects.

Incidentally, the main component of dentin is hydroxyapatite. In the mouth, elution (decalcification) of phosphate ions and calcium ions and crystallization (remineralization) to calcium phosphate and hydroxyapatite are generally in equilibrium; and dental caries is developed by acceleration of decalcification through decomposition of, for example, sucrose by bacteria such as *Streptococcus mutans* to generate organic acids, lower the pH, and elute calcium and others from the tooth. In the early stage of dental caries, a subsurface decalcification lesion called a white spot, occurs on the enamel. Here, fluoride ions, which accelerate crystallization of calcium ions and phosphate ions, i.e., remineralization to prevent occurrence of dental caries and can extinguish such white spots, are known to be useful.

Accordingly, water-soluble active ingredients such as sodium fluoride, which can supply fluoride ions to teeth in the oral cavity, are also widely used as medicinal ingredients. For example, Patent Literature 3 discloses a technique for improving the retentivity of fluorine on tooth surfaces by mixing specific amounts of fatty acid amide propyl betaine, carrageenan, and a cellulose derivative such as hydroxyethyl cellulose, while containing sodium fluoride. Patent Literature 4 discloses a technique for improving adsorption of fluoride ions to teeth by using a fluoride ion-supplying compound such as sodium fluoride, an N-acylamino acid salt, and a specific sugar alcohol.
(Patent Literature 1) JP-A-2005-289917
(Patent Literature 2) JP-A-2007-45786
(Patent Literature 3) JP-A-2009-155217
(Patent Literature 4) JP-A-2014-125443

SUMMARY OF THE INVENTION

The present invention relates to an oral composition, comprising the following ingredients (A), (B), (C), and (D):
(A) 0.005 mass % or more and 2 mass or less, in terms of fluorine atoms, of one or more fluoride ion-supplying compounds selected from the group consisting of sodium fluoride, ammonium fluoride, potassium fluoride, sodium monofluorophosphate, and tin fluoride;
(B) 4 mass % or more and 30 mass % or less of a higher alcohol having 12 or more and 22 or less carbon atoms comprising (b1) cetanol and (b2) stearyl alcohol;
(C) 0.1 mass % or more and 10 mass % or less of a surfactant comprising one or more selected from the group consisting of (c1) a nonionic surfactant selected from the group consisting of sorbitan fatty acid ester and polyoxyethylene sorbitan fatty acid ester, and (c2) an anionic surfactant being a fatty acid having 12 or more and 22 or less carbon atoms or a salt thereof; and
(D) water
wherein, the content of the ingredient (c1) is 0.05 mass % or more; a mass ratio of the content of the ingredient (A) in terms of fluorine atoms to the content of the ingredient (B), (A)/(B), is 0.002 or more and 0.2 or less; and the molar amount of (E) a polyvalent metal compound other than the ingredient (A) is less than 0.1-fold the molar amount of the ingredient (A).

Although an increase in the concentration of fluoride ions is conceivable for incorporating fluoride ions into tooth enamel and accelerating remineralization, it is difficult to contain a large amount of fluoride ions in a dentifrice composition from the viewpoint of solubility of fluoride ions and safety. As also described in Patent Literatures 1 and 2, the water-soluble active ingredients such as sodium fluoride are known to have a problem that the absorbability thereof is decreased by the presence of saliva or a biofilm. However, in efficient incorporation of a small amount of fluoride ions into the enamel, the techniques described in Patent Literatures 3 and 4 still need to be improved to sufficiently increase the incorporation rate of fluoride ions.

Accordingly, the present invention relates to an oral composition having improved ability of incorporating fluoride ions into tooth enamel and an enhanced recalcification effect.

Accordingly, the present inventors variously studied and found that when an oral composition comprises a specific higher alcohol and a specific surfactant in specific amounts at a specific mass ratio, in addition to a fluoride ion-supplying compound such as sodium fluoride and water and has a restricted content of a polyvalent metal compound, the ability of incorporating fluoride ions to teeth is efficiently enhanced while using the fluoride ion-supplying compound being a water-soluble active ingredient.

According to the oral composition of the present invention, α-gel having a lamellar structure is formed, which enhances the ability of incorporating fluoride ions into, for example, tooth enamel, while using a fluoride ion-supplying compound being a water-soluble active ingredient, can effectively prevent occurrence of dental caries, and is also significantly useful for preventing or improving dentin hypersensitivity.

BRIEF DESCRIPTION OF THE DRAWING

FIG. 1 is a graph showing a diffraction X-ray intensity distribution of the α-gel formed in the composition obtained in Example 1 by wide angle X-ray diffraction.

DETAILED DESCRIPTION OF THE INVENTION

The present invention will now be described in detail.
The oral composition of the present invention comprises 0.005 mass or more and 2 mass or less, in terms of fluorine, of one or more fluoride ion-supplying compounds selected from the group consisting of sodium fluoride, ammonium fluoride, potassium fluoride, sodium monofluorophosphate, and tin fluoride as the ingredient (A). The ingredient (A) is a water-soluble compound releasing fluoride ions in an aqueous solution. In particular, sodium fluoride is preferred from the viewpoint of ability of incorporating fluoride ions into tooth enamel and the viewpoint of high solubility in water and easiness of formulation. The fluoride ion-supplying compound can provide, for example, a dental caries preventive effect, remineralization, and dentin hypersensitivity-suppressing action.

The content of the ingredient (A) in the oral composition of the present invention is 0.005 mass % or more, preferably 0.01 mass or more, more preferably 0.02 mass or more, further preferably 0.04 mass or more, in terms of fluorine atoms, from the viewpoint of sufficiently ensuring an incorporation amount of fluoride ions into tooth enamel and dentin and the viewpoint of safety. The content of the ingredient (A) in the oral composition of the present invention is 2 mass % or less, preferably 1 mass % or less, more preferably 0.5 mass % or less, in terms of fluorine atoms, from the viewpoint of, for example, safety. The content of the ingredient (A) in the oral composition of the present invention is 0.005 mass % or more and 2 mass % or less, preferably form 0.01 to 1 mass %, more preferably from 0.02 to 1 mass %, further preferably from 0.04 to 0.5 mass %, in terms of fluorine atoms.

The oral composition of the present invention comprises 4 mass % or more and 30 mass % or less of a higher alcohol having 12 or more and 22 or less carbon atoms comprising (b1) cetanol and (b2) stearyl alcohol as the ingredient (B). That is, the ingredient (B) is a higher alcohol having 12 or more and 22 or less carbon atoms including, as essential ingredients, cetanol as the ingredient (b1) and stearyl alcohol as the ingredient (b2). Such ingredient (B), together with the surfactant as the ingredient (C) described below, forms α-gel having a structure in which lamellar layers overlap each other and can impart structural viscosity to the composition. It is believed that the structural viscosity of the α-gel ensures the fluidity of the fluoride ion-supplying compound as the ingredient (A) in water as the ingredient (D) described below, and therefore the fluoride ion-supplying compound repeatedly comes into contact with teeth while flowing, and the adsorptivity and retentivity of the released fluoride ions to, for example, teeth can be satisfactorily maintained. The oral composition of the present invention thus can effectively increase the incorporation amount of fluoride ions into, for example, tooth enamel by having an appropriate viscosity while containing water that can ensure good fluidity of the ingredient (A).

The higher alcohol as the ingredient (B) is, from the viewpoint of maintaining an appropriate viscosity as an oral composition while suitably forming α-gel, a higher alcohol comprising cetanol as the ingredient (b1) and stearyl alcohol as the ingredient (b2) and has 12 or more and 22 or less carbon atoms, wherein the mass ratio of the sum of the content of the ingredient (b1) and the content of the ingredient (b2) to the content of the ingredient (B), (((b1)+(b2))/(B)), is preferably 0.85 or more, more preferably 0.9 or more, further preferably 0.92 or more and 1 or less.

The ingredient (B) other than the ingredient (b1) and the ingredient (b2) includes preferably one or more selected from the group consisting of lauryl alcohol, myristyl alcohol, and behenyl alcohol.

The mass ratio of the content of the ingredient (b1) to the content of the ingredient (b2), ((b1)/(b2)), is preferably 0.5 or more, more preferably 0.7 or more; and preferably 5 or less, more preferably 3 or less, further preferably 2 or less, further more preferably 1.7 or less, from the viewpoint of enhancing the stability as an oral composition while satisfactorily forming α-gel.

The contents of lauryl alcohol and myristyl alcohol, which are higher alcohols having 12 or more and 22 or less carbon atoms other than the ingredient (b1) and the ingredient (b2), are adjusted such that the mass ratio of the sum of the content of lauryl alcohol and the content of myristyl alcohol to the content of the ingredient (B), ((lauryl alcohol+myristyl alcohol)/(B)), is preferably 0.05 or less, more preferably 0.03 or less, further preferably 0.01 or less, from the viewpoint of taste.

The content of behenyl alcohol, which is a higher alcohol having 12 or more and 22 or less carbon atoms other than the ingredient (b1) and the ingredient (b2), is adjusted such that the mass ratio of the content of behenyl alcohol to the content of the ingredient (B), (behenyl alcohol/(B)), is preferably 0.1 or less, more preferably 0.05 or less, from the viewpoint of preventing precipitation and separation of the ingredient (B).

The content of a higher alcohol having 10 or less carbon atoms is adjusted such that the mass ratio of the content of the higher alcohol having 10 or less carbon atoms to the content of the ingredient (B), (higher alcohol having 10 or less carbon atoms/(B)), is preferably 0.1 or less, more preferably 0.01 or less, further preferably 0.005 or less, from the viewpoint of stability. Alternatively, the oral composition of the present invention further more preferably does not contain a higher alcohol having 10 or less carbon atoms.

The content of a higher alcohol having 24 or more carbon atoms is adjusted such that the mass ratio of the content of the higher alcohol having 24 or more carbon atoms to the content of the ingredient (B), (higher alcohol having 24 or more carbon atoms/(B)), is preferably 0.1 or less, more preferably 0.01 or less, further preferably 0.005 or less, from the viewpoint of stability. Alternatively, the oral composition of the present invention further more preferably does not contain a higher alcohol having 24 or more carbon atoms.

The content of the ingredient (B) in the oral composition of the present invention is 4 mass % or more, preferably 4.5 mass % or more from the viewpoint of satisfactorily forming α-gel. The content of the ingredient (8) in the oral composition of the present invention is 30 mass % or less, preferably 25 mass % or less, more preferably 20 mass % or less, further preferably 18 mass % or less, further preferably 15 mass % or less from the viewpoint of providing an appropriate viscosity and the viewpoint of ensuring the fluidity of the fluoride-supplying compound and the dispersibility of each ingredient in water as the ingredient (D) of the composition. The content of the ingredient (B) in the oral composition of the present invention is 4 mass or more and 30 mass or less, preferably 4 to 25 mass %, more preferably from 4 to 20 mass %, further preferably from 4.5 to 18 mass %, further preferably from 4.5 to 15 mass %.

In the oral composition of the present invention, the mass ratio of the content of the ingredient (A) in terms of fluorine atoms to the content of the ingredient (B), (A)/(B), is 0.001 or more and 0.2 or less. The consequently formed α-gel can effectively increase the incorporation amount of fluoride ions while satisfactorily ensuring the fluidity of the ingredient (A). The mass ratio of the content of the ingredient (A) in terms of fluorine atoms to the content of the ingredient (B), (A)/(B), is 0.001 or more, preferably 0.002 or more, more preferably 0.003 or more from the viewpoint of effectively increasing the incorporation amount of fluoride ions. The mass ratio of the content of the ingredient (A) in terms of fluorine atoms to the content of the ingredient (B), (A)/(B), is 0.2 or less, preferably 0.1 or less, more preferably 0.05 or less from the viewpoint of satisfactorily forming α-gel and ensuring the fluidity of the ingredient (A). The mass ratio of the content of the ingredient (A) in terms of fluorine atoms to the content of the ingredient (B), (A)/(B), is 0.001 or more and 0.2 or less, preferably from 0.002 to 0.1, more preferably from 0.003 to 0.05.

The oral composition of the present invention comprises, as the ingredient (C), 0.1 mass % or more and 10 mass % or less of a surfactant comprising one or more selected from the group consisting of (c1) a nonionic surfactant selected from the group consisting of sorbitan fatty acid ester and polyoxyethylene sorbitan fatty acid ester, and (C2) an anionic surfactant being a fatty acid salt having 12 or more and 22 or less carbon atoms, wherein the content of the ingredient (c1) is 0.05 mass % or more. Thus, use of a specific amount of the surfactant as the ingredient (C) comprising one or more selected from the nonionic surfactant as the ingredient (c1) and the anionic surfactant as the ingredient (c2) and comprising the ingredient (c1) in a specific amount or more further forms, together with the ingredient (B), α-gel while ensuring the fluidity of the ingredient (A) and can effectively increase the incorporation amount of fluoride ions released from the ingredient (A) into tooth enamel or dentin while providing an appropriate structural viscosity.

The ingredient (c1) is a nonionic surfactant selected from the group consisting of sorbitan fatty acid ester and polyoxyethylene sorbitan fatty acid ester.

The sorbitan fatty acid ester is, for example, one or more selected from preferably those derived from a fatty acid having 10 or more carbon atoms, more preferably those derived from a fatty acid having 12 or more carbon atoms; and preferably those derived from a fatty acid having 20 or less carbon atoms, more preferably those derived from a fatty acid having 18 or less carbon atoms, from the viewpoint of the ability of incorporating fluoride ions released from the ingredient (A) into teeth. Specifically, for example, examples of the sorbitan fatty acid ester include one or more selected from the group consisting of sorbitan monocaprylate, sorbitan monoundecylate, sorbitan monolaurate, sorbitan monotridecylate, sorbitan monomyristate, sorbitan monopalmitate, sorbitan monooleate, sorbitan trioleate, sorbitan tetraoleate, sorbitan sesquioleate, sorbitan monostearate, and sorbitan tristearate. Among these examples, preferred are one or more selected from the group consisting of sorbitan monooleate, sorbitan sesquioleate, sorbitan monostearate, and sorbitan monopalmitate; and more preferred are one or more selected from the group consisting of sorbitan monooleate, sorbitan sesquioleate, and sorbitan monostearate.

The polyoxyethylene sorbitan fatty acid ester is, for example, one or more selected from preferably those derived from a fatty acid having 6 or more carbon atoms, more preferably those derived from a fatty acid having 12 or more carbon atoms; and preferably those derived from a fatty acid having 22 or less carbon atoms, more preferably those derived from a fatty acid having 20 or less carbon atoms, from the viewpoint of the ability of incorporating fluoride ions released from the ingredient (A) into teeth. The average number of moles of the ethyleneoxy group added in the polyoxyethylene sorbitan fatty acid ester is, from the same viewpoint, preferably from 5 to 40 moles, more preferably from 10 to 25 moles, further preferably from 10 to 20 moles. Examples of a polyoxyethylene sorbitan fatty acid ester include one or more selected from the group consisting of polyoxyethylene sorbitan monolaurate, polyoxyethylene sorbitan monomyristate, polyoxyethylene sorbitan monopalmitate, polyoxyethylene sorbitan monostearate, and polyoxyethylene sorbitan monooleate. Among these examples, preferred are one or more selected from the group consisting of polyoxyethylene sorbitan monopalmitate, polyoxyethylene sorbitan monostearate, and polyoxyethylene sorbitan monooleate, from the viewpoint of enhancing low-temperature stability while showing excellent foamability.

The anionic surfactant as the ingredient (c2) is a fatty acid having 12 or more and 22 or less carbon atoms or a salt thereof. The ingredient (c2) has 12 or more carbon atoms, preferably 14 or more carbon atoms, more preferably 16 or more carbon atoms, and 22 or less carbon atoms, preferably 20 or less carbon atoms, more preferably 18 or less carbon atoms, from the viewpoint of the ability of incorporating fluoride ions released from the ingredient (A) into teeth and the viewpoint of ensuring good flavor. Although the fatty acid constituting the ingredient (c2) may be a linear chain or may be a branched chain, the fatty acid is preferably a linear chain from the viewpoint of the ability of incorporating fluoride ions released from the ingredient (A) into teeth. Specifically, examples of the ingredient (c2) include one or more selected from the group consisting of lauric acid, myristic acid, palmitic acid, stearic acid, coconut oil fatty acid, and salts thereof. Among these examples, preferred are one or more selected from the group consisting of myristic acid, palmitic acid, stearic acid, and salts thereof; and it is further preferred that stearic acid or a salt thereof is at least included as the ingredient (c2). Examples of the salt constituting the ingredient (c2) include alkali metals selected from the group consisting of sodium and potassium; basic amino acids, such as arginine; alkanolammoniums, such as monoethanolammonium, diethanolammonium, and triethanolammonium; and ammonium. Among these examples, the salt constituting the ingredient (c2) is preferably an alkali metal selected from the group consisting of sodium and potassium from the viewpoint of stability.

The ingredient (C) comprises one or more selected from the group consisting of the above-mentioned ingredient (c1) and ingredient (c2) and may further comprise one or more selected from the group consisting of (c3) a nonionic surfactant selected from the group consisting of polyoxyethylene hydrogenated castor oil, sucrose fatty acid ester, and polyglycerol fatty acid ester, and (c4) an anionic surfactant selected from the group consisting of sodium alkylsulfate, acyl methyl taurine salts, and acyl sarcosine salts. That is, the oral composition of the present invention comprises one or more selected from a nonionic surfactant of the ingredient (c1) and an anionic surfactant of the ingredient (c2) as the surfactant of the ingredient (C), and can further comprise the ingredient (c3) as a nonionic surfactant other than the ingredient (c1), or the ingredient (c4) as an anionic surfactant other than the ingredient (c2).

The average of moles the ethyleneoxy group added in the polyoxyethylene hydrogenated castor oil as the ingredient (c3) is preferably from 20 to 100 moles, more preferably from 40 to 80 moles, from the viewpoint of ensuring the stability of the composition while satisfactorily maintaining the ability of incorporating fluoride ions released from the ingredient (A) into teeth. The content of the polyoxyethylene hydrogenated castor oil of the ingredient (c3) in the oral composition of the present invention is preferably 0.5 mass or less, more preferably 0.3 mass % or less, further preferably 0.1 mass or less, further more preferably 0.01 mass or less from the viewpoint of satisfactorily maintaining the ability of incorporating fluoride ions released from the ingredient (A) into teeth. Alternatively, the oral composition of the present invention need not contain polyoxyethylene hydrogenated castor oil.

Examples of the polyglycerol fatty acid ester of the ingredient (c3) include those in which one to four fatty acid molecules having 8 to 24 carbon atoms are ester-bonded to polyglycerin composed of 2 to 20 condensed glycerin molecules. The fatty acid moiety constituting the polyglycerol fatty acid ester is preferably derived from a fatty acid having 12 to 20 carbon atoms, more preferably derived from a fatty acid having 12 to 18 carbon atoms, further preferably derived from a fatty acid having 12 to 14 carbon atoms, from the viewpoint of ensuring the stability of the composition while satisfactorily maintaining the ability of incorporating fluoride ions released from the ingredient (A) into teeth, and the polyglycerol fatty acid ester is preferably a monoester composed of these fatty acid moieties. The average degree of condensation of glycerin in the polyglycerol fatty acid ester is, from the same viewpoint, preferably from 2 to 20, more preferably from 5 to 12.

Examples of the sucrose fatty acid ester of the ingredient (c3) include sucrose fatty acid ester composed of fatty acid moiety derived from a fatty acid having 6 to 20 carbon atoms. Among these examples, the fatty acid moiety constituting the sucrose fatty acid ester is preferably derived from a fatty acid having 10 to 18 carbon atoms, more preferably derived from a fatty acid having 12 to 14 carbon atoms, from the viewpoint of ensuring the stability of the composition while satisfactorily maintaining the ability of incorporating fluoride ions released from the ingredient (A) into teeth and the viewpoint of providing good feeling upon use.

The one or more anionic surfactants selected from the group consisting of alkyl sulfates, acyl methyl taurine salts, and acyl sarcosine salts as the ingredient (c4) are, for example, one or more selected from alkyl sulfates such as sodium lauryl sulfate and sodium myristyl sulfate; sodium or potassium salts of acyl sarcosine such as N-lauroyl sarcosine, N-myristoyl sarcosine, N-palmitoyl sarcosine, N-stearoyl sarcosine, N-isostearoyl sarcosine, and N-oleoyl sarcosine; and sodium or potassium salts of acyl methyl taurine such as capryl methyl taurine, lauryl methyl taurine, myristyl methyl taurine, palmityl methyl taurine, and stearyl methyl taurine. Among these examples, preferred are one or more selected from the group consisting of sodium lauryl sulfate, N-lauroyl sarcosine salts, N-myristoyl sarcosine salts, lauryl methyl taurine salts, and myristyl methyl taurine salts; and more preferred is sodium lauryl sulfate.

The content of the ingredient (c1) in the oral composition of the present invention is 0.05 mass % or more, preferably 0.2 mass % or more, more preferably 0.4 mass % or more, further preferably 0.5 mass % or more, further preferably 1 mass % or more from the viewpoint of effectively enhancing the ability of incorporating fluoride ions released from the ingredient (A) into teeth while forming, together with the ingredient (B), α-gel and providing an appropriate structural viscosity; and is 10 mass % or less, preferably 8 mass % or less, more preferably 6 mass % or less from the viewpoint of ensuring the stability of the composition and the viewpoint of an appropriate viscosity and balance with flavor.

When the ingredient (c2) is not contained, the content of the ingredient (c1) in the oral composition of the present invention is 0.05 mass % or more, preferably 1 mass % or more, more preferably 1.5 mass % or more, further preferably 2 mass % or more from the viewpoint of effectively enhancing the ability of incorporating fluoride ions released from the ingredient (A) into teeth while forming, together with the ingredient (B), α-gel and providing an appropriate structural viscosity. When the ingredient (c2) is contained, the content of the ingredient (c1) in the oral composition of the present invention is 0.05 mass % or more, preferably 0.1 mass % or more, more preferably 0.2 mass % or more, further preferably 0.4 mass % or more, further preferably 0.5 mass or more from the viewpoint of effectively enhancing the ability of incorporating fluoride ions released from the ingredient (A) into teeth while forming, together with the ingredient (B), α-gel and providing an appropriate structural viscosity. When the ingredient (c2) is not contained, the mass ratio of the content of the ingredient (B) to the content of the ingredient (c1), (B)/(c1), is preferably 1 or more, more preferably 1.2 or more, further preferably 1.4 or more from the viewpoint of effectively enhancing the ability of incorporating fluoride ions released from the ingredient (A) into teeth while forming, together with the ingredient (B), α-gel and providing an appropriate structural viscosity. When the ingredient (c2) is not contained, the mass ratio of the content of the ingredient (B) to the content of the ingredient (c1), (B)/(c1), is preferably 10 or less, more preferably 7 or less, further preferably 5 or less, further preferably 3.5 or less from the viewpoint of ensuring the stability of the composition and the viewpoint of an appropriate viscosity and balance with flavor.

When the ingredient (c2) is contained, the content of the ingredient (c1) in the oral composition is preferably 5 mass or less.

The content of the ingredient (c2) in the oral composition of the present invention is preferably 0.05 mass % or more, more preferably 0.08 mass % or more, further preferably 0.1 mass % or more in terms of fatty acids from the viewpoint of effectively enhancing the ability of incorporating fluoride ions released from the ingredient (A) into teeth while forming, together with the ingredient (B) and the ingredient (c1), α-gel and providing an appropriate structural viscosity, and is more preferably 0.2 mass % or more, further preferably 0.4 mass % or more from the viewpoint of forming, together with the ingredient (B), α-gel and effectively enhancing the ability of incorporating fluoride ions released from the ingredient (A) into teeth and the viewpoint of providing an appropriate viscosity. The content of the ingredient (c2) in the oral composition of the present invention is preferably 5 mass % or less, more preferably 3 mass % or less, further preferably 2.5 mass % or less, further preferably 2 mass % or less in terms of fatty acids from the viewpoint of ensuring the stability of the composition, the viewpoint of an appropriate viscosity and balance with flavor, and the viewpoint of reducing harm to the oral mucosa; and is preferably 0.5 mass % or less, more preferably 0.2 mass % or less from the viewpoint of further improving the flavor. Alternatively, the oral composition of the present invention need not contain the ingredient (c2).

The sum of the content of the ingredient (c1) and the content of the ingredient (c2) in terms of fatty acids in the oral composition of the present invention is preferably 0.1 mass % or more, more preferably 0.2 mass % or more, further preferably 0.5 mass % or more, further preferably 1 mass % or more from the viewpoint of effectively enhancing the ability of incorporating fluoride ions released from the ingredient (A) into teeth while forming, together with the ingredient (B), α-gel and ensuring an appropriate viscosity; and is preferably 10 mass % or less, more preferably 8 mass % or less, further preferably 6.5 mass % or less from the viewpoint of ensuring the stability of the composition and the viewpoint of an appropriate viscosity and balance with flavor. The oral composition of the present invention preferably contains both the ingredient (c1) and the ingredient (c2) from the viewpoint of being capable of further improving the ability of incorporating fluoride ions into teeth by a combination of the ingredient (c1) and the ingredient (c2).

When both the ingredient (c1) and the ingredient (c2) are contained, the mass ratio of the content of the ingredient (B) to the content of the ingredient (c1), (B)/(c1), is preferably 1 or more, more preferably 1.2 or more, further preferably 1.4 or more from the viewpoint of effectively enhancing the ability of incorporating fluoride ions released from the ingredient (A) into teeth while forming, together with the ingredient (B), α-gel and providing an appropriate structural viscosity. When both the ingredient (c1) and the ingredient (c2) are contained, the mass ratio of the content of the ingredient (B) to the content of the ingredient (c1), (B)/(c1), is preferably 20 or less, more preferably 17 or less, further preferably 15 or less from the viewpoint of ensuring the stability of the composition and the viewpoint of an appropriate viscosity and balance with flavor. When both the ingredient (c1) and the ingredient (c2) are contained, the mass ratio of the content of the ingredient (B) to the content of the ingredient (c1), (B)/(c1), is preferably from 1 to 20, more preferably from 1.2 to 17, further preferably from 1.4 to 15, or from 1 or more to 10 or less.

In addition, when both the ingredient (c1) and the ingredient (c2) are contained, the mass ratio of the content of the ingredient (B) to the content of the ingredient (c2), (B)/(c2), is preferably 2 or more, more preferably 4 or more, further preferably 5 or more from the viewpoint of effectively enhancing the ability of incorporating fluoride ions released from ingredient (A) into teeth while forming, together with the ingredient (B), α-gel and providing an appropriate structural viscosity. When both the ingredient (c1) and the ingredient (c2) are contained, the mass ratio of the content of the ingredient (B) to the content of the ingredient (c2), (B)/(c2), is preferably 180 or less, more preferably 150 or less, further preferably 100 or less, further preferably 90 or less from the viewpoint of ensuring the stability of the composition and the viewpoint of an appropriate viscosity and balance with flavor. When both the ingredient (c1) and the ingredient (c2) are contained, the mass ratio of the content of the ingredient (B) to the content of the ingredient (c2), (B)/(c2), is from 2 to 180, more preferably form 4 to 150, further preferably form 5 to 100, further preferably from 5 to 90.

The content of the ingredient (c3) in the oral composition of the present invention is preferably 0.5 mass % or less, more preferably 0.25 mass % or less, further preferably 0.2 mass % or less, further preferably 0.1 mass % or less, further preferably 0.05 mass % or less from the viewpoint of increasing the ability of incorporating fluoride ions released from the ingredient (A) into teeth and the viewpoint of ensuring the ability of incorporating and balance with flavor.

The content of the ingredient (c4) in the oral composition of the present invention is preferably 2 mass % or less, more preferably 1.5 mass % or less, further preferably 1 mass % or less, further preferably 0.7 mass % or less from the viewpoint of harm on the gums and oral mucosa, and the viewpoint of flavor.

The content of the ingredient (C) in the oral composition of the present invention is 0.1 mass % or more, preferably 0.2 mass or more, more preferably 0.3 mass % or more, further more preferably 0.5 mass % or more from the viewpoint of effectively increasing the ability of incorporating fluoride ions released from the ingredient (A) into teeth while forming, together with the ingredient (B), α-gel and ensuring an appropriate viscosity. The content of the ingredient (C) in the oral composition of the present invention is 10 mass % or less, preferably 8 mass % or less, more preferably 7 mass % or less, further preferably 6.5 mass % or less from the viewpoint of ensuring the stability of the composition and the viewpoint of an appropriate viscosity and balance with flavor. The content of the ingredient (C) in the oral composition of the present invention is 0.1 mass or more and 10 mass % or less, preferably form 0.2 to 8 mass %, more preferably form 0.3 to 7 mass %, further preferably from 0.5 to 6.5 mass %.

When the oral composition of the present invention comprises the ingredient (c1) as the ingredient (C), the mass ratio of the content of the ingredient (B) to the content of the nonionic surfactant including the ingredient (c1), ((B)/nonionic surfactant), is preferably 1 or more, more preferably 1.2 or more, further preferably 1.4 or more from the viewpoint of satisfactorily forming α-gel and increasing the ability of incorporating fluoride ions released from the ingredient (A) into teeth. The mass ratio of the content of the ingredient (B) to the content of the nonionic surfactant including the ingredient (c1), ((B)/nonionic surfactant), is preferably 20 or less, more preferably 17 or less, further preferably 15 or less from the viewpoint of maintaining an appropriate viscosity as an oral composition and the viewpoint of stability. The mass ratio of the content of the ingredient (B) to the content of the nonionic surfactant including the ingredient (c1), ((B)/nonionic surfactant), is preferably from 1 to 20, more preferably from 1.2 to 17, further preferably from 1.4 to 15.

When the oral composition of the present invention comprises the ingredient (c2) as the ingredient (C), the mass ratio of the content of the ingredient (B) to the content of the anionic surfactant including the ingredient (c2), ((B)/anionic surfactant), is preferably 4 or more, more preferably 5 or more, further preferably 7 or more, further preferably 10 or more from the viewpoint of satisfactorily forming α-gel and increasing the ability of incorporating fluoride ions released from the ingredient (A) into teeth. The mass ratio of the content of the ingredient (B) to the content of the anionic surfactant including the ingredient (c2), ((B)/anionic surfactant), is preferably 180 or less, more preferably 100 or less, further preferably 90 or less from the viewpoint of ensuring stability while maintaining an appropriate viscosity as an oral composition and the viewpoint of providing good feeling upon use. The mass ratio of the content of the ingredient (B) to the content of the anionic surfactant including the ingredient (c2), ((B)/anionic surfactant), is preferably from 4 to 180, more preferably from 5 to 180, further more preferably from 5 to 100, further preferably from 7 to 100, further preferably from 10 to 90.

In the oral composition of the present invention, the mass ratio of the content of the ingredient (B) to the sum of the content of the ingredient (c1) and the content of the ingredient (c2) in terms of fatty acids, ((B)/((c1)+(c2))), is preferably higher than 1, more preferably 1.2 or more, further preferably 1.5 or more from the viewpoint of satisfactorily forming α-gel and increasing the ability of incorporating fluoride ions released from the ingredient (A) into teeth. The mass ratio of the content of the ingredient (B) to the sum of the content of the ingredient (c1) and the content of the ingredient (c2) in terms of fatty acids, ((B)/((c1)+(c2))), is preferably 40 or less, more preferably 35 or less, further preferably 30 or less, further preferably 15 or less from the viewpoint of ensuring stability while maintaining an appropriate viscosity as an oral composition and the viewpoint of providing good feeling upon use. The mass ratio of the content of the ingredient (B) to the sum of the content of the ingredient (c1) and the content of the ingredient (c2) in the terms of fatty acids, ((B)/((c1)+(c2))), is preferably more than 1 and 40 or less, more preferably from 1.2 to 35, further preferably from 1.5 to 30, further preferably from 1.5 to 15.

It is preferred to restrict inclusion of a cationic surfactant other than a cationic bactericide in the oral composition of the present invention from the viewpoint of preventing harm on the oral mucosa. The content of the cationic surfactant other than the cationic bactericide in the oral composition of the present invention is preferably 0.1 mass % or less, more preferably 0.05 mass or less, further preferably 0.01 mass % or less. Alternatively, the oral composition of the present invention preferably does not contain the cationic surfactant other than the cationic bactericide. Examples of the cationic bactericide include one or more selected from the group consisting of a quaternary ammonium compound and a biguanide compound. Examples of the quaternary ammonium compound include cetyl pyridinium chloride, benzethonium chloride, benzalkonium chloride, stearyl dimethyl ammonium chloride, stearyl trimethyl ammonium chloride, cetyl trimethyl ammonium chloride, methyl benzethonium chloride, lauryl trimethyl ammonium chloride, and lauroyl colamino formyl methyl pyridinium chloride. Examples of the biguanide compound include chlorhexidine and its salts such as chlorhexidine gluconate and chlorhexidine hydrochloride.

The oral composition of the present invention comprises water as the ingredient (D). The term "water" of the ingredient (D) in the present invention refers to the total water in the oral composition comprising not only, for example, purified water blended to the oral composition but also the water contained in each of the blended ingredients, such as a 70% sorbitol liquid (aqueous solution) and a 48% potassium hydroxide liquid (aqueous solution) used in prescribing. The oral composition thus-containing water as the ingredient (I)) can satisfactorily disperse or dissolve each ingredient and improve a good feeling upon use and the ability of incorporating fluoride ions released from the ingredient (A) into teeth, while ensuring an appropriate viscosity and good shape-retainability as an oral composition and satisfactorily maintaining the formed α-gel in the composition. The content of the ingredient (D) in the oral composition of the present invention is preferably 50 mass % or more, more preferably 55 mass % or more; and preferably 95 mass % or less, more preferably 92 mass or less, further preferably 80 mass % or less. The content of the ingredient (D) in the oral composition of the present invention is preferably from 50 to 95 mass %, more preferably from 55 to 92 mass %, further preferably from 55 to 80 mass %.

The content of the ingredient (D), i.e., the water content in the oral composition of the present invention can be calculated from the content of the blended water and the content of water in the blended ingredients, and the content can also be measured with, for example, Karl Fischer moisture titrator. As the Karl Fischer moisture titrator, for example, a trace moisture measuring device (Hiranuma Sangyo Co., Ltd.) can be used. By using this device, 5 g of an oral composition is suspended in 25 g of anhydrous methanol, and the water content in 0.02 g of this suspension can be measured.

In the oral composition of the present invention, the molar amount of (E) a polyvalent metal compound other than the ingredient (A) is less than 0.1-fold the molar amount of the ingredient (A). Consequently, this prevents that the ingredient (A) and a polyvalent metal ion released from the ingredient (E) form a metal fluoride in the composition, suppresses that the α-gel formed by the ingredients (B) and (C) is collapsed, and further prevents that a metal salt is precipitated by binding the ingredient (c2) and a polyvalent metal of the ingredient (F) when the ingredient (c2) is contained, to thereby allow fluoride ions to be released when the composition is applied to the oral cavity. Accordingly, a reduction in the ability of incorporation into, for example, tooth enamel can be effectively suppressed.

Examples of the ingredient (E) include compounds releasing polyvalent metal ions such as calcium ions, magnesium ions, aluminum ions, zinc ions, copper ions, and manganese ions, in an aqueous solution and specifically, for example, polyvalent metal ion-supplying compounds being water-soluble compounds having a solubility in 100 mL of water at 20° C. of more than 0.1 g/100 mL, such as metal sulfates, metal gluconates, metal lactates, metal glycerophosphates, and chlorides;

abrasives (abrasive powders) containing polyvalent metals such as aluminum, calcium, zirconium, iron, copper, zinc, and manganese, e.g., water-insoluble calcium compounds such as calcium carbonate, calcium hydrogen phosphate, insoluble potassium metaphosphate, aluminum silicate, zirconium silicate, aluminum oxide, aluminum hydroxide, and zinc oxide; and sparingly water-soluble polyvalent metal compounds being a solid powder at 20° C., and having a solubility in 100 mL of water at 20° C. of 0.1 g/100 mL or less, e.g., polyvalent metal compounds selected from the group consisting of strontium, magnesium, aluminum, calcium, zirconium, iron, copper, zinc, and manganese.

However, chlorophyll compounds such as sodium copper chlorophyll and sodium iron chlorophyll stably contain polyvalent metal ions in their molecules and are therefore not liable to release polyvalent metal ions and also not liable to generate a precipitate due to a polyvalent metal. Accordingly, in the present specification, the chlorophyll compounds are not encompassed in the ingredient (E). Consequently, the chlorophyll compounds can be contained in the oral composition of the present invention in an amount of preferably from 0.001 to 0.5 mass %, more preferably from 0.01 to 0.1 mass % as needed.

The molar amount of (E) the polyvalent metal compound other than the ingredient (A) is less than 0.1-fold, preferably 0.05-fold or less, more preferably 0.01-fold or less the molar amount of the ingredient (A) from the viewpoint of effectively releasing fluoride ions and suppressing collapse of the formed α-gel when the composition is applied to the oral cavity. Alternatively, the oral composition of the present invention preferably does not contain ∈ the polyvalent metal compound other than the ingredient (A), except for inevitable contamination.

The content of (E) the polyvalent metal compound in the oral composition of the present invention is preferably 0.1 mass % or less, preferably 0.01 mass % or less, more preferably 0.001 mass % or less in terms of metal atom. Alternatively, the oral composition of the present invention preferably does not contain the ingredient (E), except for inevitable contamination.

In the oral composition of the present invention, the mass ratio of the content of (F) oil other than the ingredient (B), the ingredient (C), an oil-soluble medicinal ingredient, and a flavoring agent to the content of the ingredient (B), (F)/(B), is preferably less than 1. In the oral composition of the present invention, the restriction of the content of (F) the oil with respect to the content of the ingredient (B) can improve the stability of the oral composition within the limited range of the surfactant that can be blended in the composition, can effectively prevent inhibition of α-gel formation by the ingredients (B) and (C), and can provide good flavor. Examples of the ingredient (F) include hydrocarbon oils such as liquid paraffin, vaseline, mineral oil, light liquid paraffin, paraffin wax, ceresin, microcrystalline wax, carnauba wax, bees wax, squalane, and squalene; ester oils such as isopropyl myristate, isopropyl palmitate, propyl adipate, diethyl sebacate, and glycerol fatty acid ester; triglycerides and vegetable oils containing it such as olive oil, rapeseed oil, shea butter, and rice bran oil; silicone oil; preservatives such as methyl parahydroxybenzoate and ethyl parahydroxybenzoate; and oil-soluble bactericides.

Examples of the oil-soluble medicinal ingredient include β-glycyrrhetinic acid, tocopherol, azulene, triclosan, isopropylmethylphenol, and thymol. In the present specification, these oil-soluble medicinal ingredients are not encompassed in the oil as the ingredient (F). Consequently, the oil-soluble medicinal ingredient can be contained in the oral composition of the present invention in an amount of preferably from 0.01 to 3.5 mass %, more preferably from 0.1 to 2.5 mass % as needed.

The mass ratio of the content of the ingredient (F) to the content of the ingredient (B), ((F)/(B)), is preferably less than 1, more preferably 0.5 or less, further preferably 0.3 or less.

The content of the ingredient (F) in the oral composition of the present invention is preferably 5 mass % or less, more preferably 2 mass % or less, further preferably 1 mass % or less, further preferably 0.5 mass % or less. When the ingredient (F) is an oil that is a liquid at 25° C., the content of the ingredient (F) in the oral composition of the present invention is preferably 5 mass % or less, further preferably 3 mass % or less, further preferably 2 mass % or less.

It is preferred to restrict inclusion of a cellulose binder in the oral composition of the present invention from the viewpoint of maintaining an appropriate viscosity and shape-retainability as an oral composition due to the formed α-gel and ensuring excellent ability of incorporating fluoride ions released from the ingredient (A) into teeth. Examples of the cellulose binder include sodium carboxymethyl cellulose and hydroxyalkyl cellulose (e.g., hydroxyethyl cellulose and hydroxypropyl cellulose). The content of the cellulose binder in the oral composition of the present invention is preferably 0.3 mass % or less, more preferably 0.25 mass % or less, further preferably 0.2 mass % or less, further more preferably 0.1 mass % or less. Alternatively, the oral cavity composition of the present invention preferably does not contain a cellulose binder excluding inevitable contamination.

The oral composition of the present invention can comprise a binder other than the cellulose binder. The binder other than the cellulose binder is, for example, one or more selected from the group consisting of sodium alginate, carrageenan, xanthan gum, sodium polyacrylate, pectin, agar, gum tragacanth, gum arabic, guar gum, karaya gum, locust bean gum, gellan gum, tamarind gum, and *psyllium* seed gum, and carboxyvinyl polymers, and is preferably one or more selected from carrageenan and xanthan gum.

The content of the binder other than the cellulose binder in the oral composition of the present invention is preferably 0.3 mass % or less, more preferably 0.2 mass % or less, further preferably 0.1 mass % or less from the viewpoint of enhancing the ability of incorporating fluoride ions into teeth. Alternatively, the oral composition of the present invention need not contain the binder other than the cellulose binder.

As the carboxyvinyl polymer, commercially available products, such as Carbopol 940, 941 (Lubrizol Advanced Materials, Inc.), can be used. However, it is preferred to further restrict inclusion of such a carboxyvinyl polymer. Specifically, the content of the carboxyvinyl polymer in the oral composition of the present invention is preferably 0.3 mass % or less, more preferably 0.2 mass % or less, further preferably 0.1 mass % or less. Alternatively, the oral composition of the present invention need not contain the carboxyvinyl polymer.

The oral composition of the present invention can further comprise a thickener from the viewpoint of enhancing the viscoelasticity of the binder. Examples of the thickener is preferably one or more selected from thickening silica having an oil absorption of 180 to 350 mL/100 g and dextrin fatty acid. The content of the thickening silica in the oral composition of the present invention is preferably 5 mass % or less, more preferably 3 mass % or less, further preferably 2 mass % or less from the viewpoint of ensuring the ability of incorporating fluoride ions into teeth. The content of the dextrin fatty acid in the oral composition of the present invention is preferably 3 mass % or less, more preferably 1.5 mass % or less from the viewpoint of increasing the ability of incorporating fluoride ions into teeth and the viewpoint of balance with flavor. The fatty acid dextrin is preferably dextrin palmitate.

The oral composition of the present invention can comprise abrasive silica having an oil absorption of 50 to 150 mL/100 g. The content of the abrasive silica is preferably restricted from the viewpoint of ensuring the ability of incorporating fluoride ions released from the ingredient (A) in water as the ingredient (D) into teeth while suppressing absorption of the water as the ingredient (D) and maintaining an appropriate structural viscosity due to the α-gel formed by the ingredient (B) and the ingredient (C). The abrasive silica is abrasive other than the above-mentioned abrasive (abrasive powder) containing a polyvalent metal and is a water-absorbing ingredient that is solid at 20° C. The content of the abrasive silica in the oral composition of the present invention is preferably 7 mass % or less, more preferably 5 mass % or less, further preferably 3 mass % or less, further preferably 2 mass % or less, further preferably 1 mass % or less from the viewpoint of increasing the ability of incorporating fluoride ions into teeth. Alternatively, the oral composition of the present invention need not contain the abrasive silica having an oil absorption of 50 to 150 mL/100 g.

The term "oil absorption" refers to the amount of oil that can be supported by silica and means a value defined by the amount of absorbed boiled linseed oil measured by a method according to JIS K5101-13-2 (established in 2004).

It is preferred that the oral composition of the present invention further comprises a sugar alcohol from the viewpoint of flavor. The content of the sugar alcohol is preferably 30 mass % or less, more preferably 20 mass % or less, further preferably 15 mass % or less from the viewpoint of increasing the ability of incorporating fluoride ions released from the ingredient (A) into teeth; and is preferably 1 mass % or more, more preferably 2 mass % or more, further preferably 5 mass % or more from the viewpoint of flavor. Examples of the sugar alcohol is preferably one or more selected from the group consisting of sorbitol, xylitol, erythritol, reduced palatinose, and mannitol, more preferably one or more selected from the group consisting of sorbitol and xylitol from the viewpoint of high solubility in water and providing a smooth feel to the composition. The composition preferably at least comprises sorbitol as the sugar alcohol.

However, since sorbitol and xylitol are water-absorbing ingredients that are solid at 20° C., like the abrasive silica, it is preferred to restrict the total content of the water-absorbing ingredients from the viewpoint of ensuring the ability of incorporating fluoride ions released from the ingredient (A) in water as the ingredient (D) into teeth while suppressing the absorption of the water as the ingredient (D) and maintaining an appropriate viscosity due to the α-gel formed by the ingredient (B) and ingredient (C). Specifically, the total content of the water-absorbing ingredients being solid at 20° C. and selected from the group consisting of abrasive silica, sorbitol, and xylitol in the oral composition of the present invention is preferably 35 mass % or less, more preferably 30 mass % or less, further preferably 25 mass % or less, further preferably 20 mass % or less.

It is preferred to restrict inclusion of ethanol in the oral composition of the present invention from the viewpoint of effectively preventing the α-gel formed by the ingredients (B) and (C) from collapsing and maintaining the ability of incorporating fluoride ions released from the ingredient (A) into teeth, the viewpoint of ensuring an appropriate viscosity, and the viewpoint of suppressing irritation. Specifically, the content of ethanol in the oral composition of the present invention is preferably 8 mass % or less, more preferably 5 mass % or less, further preferably 2 mass % or less. Alternatively, the oral composition of the present invention preferably does not contain ethanol.

The oral composition of the present invention can comprise, in addition to the above-mentioned ingredients, for example, a polyhydric alcohol, a sweetener, a humectant, a preservative, a fluoride, an enzyme, and a dye within a range not impairing the advantageous effects of the present invention.

The viscosity at 20° C. of the oral composition of the present invention is preferably 5,000 dPa·s or less, more preferably 4,000 dPa·s or less, further preferably 3,800 dPa·s or less; and preferably 300 dPa·s or more, more preferably 400 dPa·s or more, further preferably 500 dPa·s or more, further preferably dPa·s or more from the viewpoint of maintaining an appropriate viscosity and exerting excellent ability of incorporating fluoride ions released from the ingredient (A) into teeth and the viewpoint of ensuring good shape-retainability and feeling upon use. The viscosity at 20° C. of the oral composition of the present invention is preferably 5,000 dPa·s or less, more preferably from 300 to 5,000 dPa·s, further preferably from 400 to 4,000 dPa·s, further preferably from 500 to 3,500 dPa·s, further preferably from 700 to 3,500 dPa·s. Such a viscosity can be measured using a composition filled in a chamber for viscosity measurement and preserved in an incubator of 20° C. for 24 hours with a Helipath viscometer (VISCOMETER TVB-10, Toki Sangyo Co., Ltd.) and a rotor T-C at a rotation speed of 2.5 rpm for 1 minute.

Examples of the form of the oral composition of the present invention include toothpaste, a coating agent, a mouthwash, and a liquid dentifrice. Among these, a liquid dentifrice and toothpaste are preferred from the viewpoint of sufficiently supplying the oral composition of the present invention to the gums or oral mucosa and effectively incorporating fluoride ions released from the ingredient (A) into, for example, tooth enamel. The oral composition of the present invention is preferably used by applying the composition to the oral cavity and, after the application, rinsing the oral cavity with water. Even if the oral cavity is rinsed with water after the application, fluoride ions can be effectively incorporated into teeth. Methods for application to the oral cavity may be coating, brushing with a toothbrush, or gargling, and coating or brushing with a toothbrush is preferred.

The method of producing the oral composition of the present invention comprises a step (I) of mixing a mixture liquid containing the ingredient (B) and the ingredient (C) at a temperature not lower than the melting point of the ingredient (B) and not higher than 90° C. and a step (II) of adding thereto the ingredient (A). Specifically, the method preferably comprises a step (I-X) described below and the step (II) from the viewpoint of effectively enhancing the ability of incorporating fluoride ions released from the ingredient (A) into teeth. Alternatively, the method preferably comprises a step (I-Y) described below and the step (II) from the viewpoint of effectively enhancing the ability of incorporating fluoride ions released from the ingredient (A) into teeth and the viewpoint of simplifying the production facilities.

The production method comprising the step (I-X) and the step (II) is a method comprising a step (I-X) of mixing a mixture liquid 1-1 containing the ingredient (B) and the ingredient (C) at a temperature not lower than the melting point of the ingredient (B) and not higher than 90° C. and then adding the ingredient (D) to and mixed with the resulting mixture liquid 1-1 to prepare a mixture liquid 1-2 and a step (II) of adding thereto the ingredient (A). In this production method, the ingredient (A) may be added to and mixed with the mixture liquid 1-2 prepared through the step (I-X) or may be, together with the ingredient (D), added to and mixed with the mixture liquid 1-1. The ingredient (D) may be partially mixed with the mixture liquid 1-1. When the ingredient (C) contains the ingredient (c2), it is preferred to mix a part of the ingredient (D) with the mixture liquid 1-1. In such a case, preferably, the ingredient (A) is added to the remaining ingredient (D), and the resulting mixture is added to and mixed with the mixture liquid 1-1 to prepare the mixture liquid 1-2. The temperature of mixing the mixture liquid 1-1 and the temperature of the step of preparing the mixture liquid 1-2 may be a temperature not lower than the melting point of the ingredient (B) and not higher than 90° C. and is a temperature not lower than the melting point that is the highest in the ingredient (B), more preferably a temperature not lower than the melting point of the ingredient (B) and not higher than 85° C., further preferably a temperature not lower than 80° C. and not higher than 85° C. The temperature not lower than the melting point of the ingredient (B) is preferably 65° C. or more, more preferably 75° C. or more, further preferably 80° C. or more.

The production method comprising the step (I-Y) and the step (II) is a method comprising a step (I-Y) of mixing a mixture liquid 2 containing the ingredients (B) to (D) and a step (II) of adding thereto the ingredient (A). In this production method, the ingredient (A) may be added to and mixed with the mixture liquid 2 prepared through the step (I-Y) or may be added to the ingredient (D) in advance.

The oral composition of the present invention can effectively incorporate fluoride ions released from the ingredient (A) into tooth enamel or dentin and is also therefore very useful as an agent for promoting incorporation of fluoride into teeth and also useful for treatment or prevention of dentin hypersensitivity by incorporation into dentin.

With respect to the above-described embodiments, the present invention further discloses the following oral compositions, uses for oral cavities, and methods for producing them.

[1] An oral composition comprising the following ingredients (A), (B), (C), and (D):

(A) 0.005 mass % or more and 2 mass % or less, in terms of fluorine atoms, of one or more fluoride ion-supplying compounds selected from the group consisting of sodium fluoride, ammonium fluoride, potassium fluoride, sodium monofluorophosphate, and tin fluoride;

(B) 4 mass % or more and 30 mass % or less of a higher alcohol having 12 or more and 22 or less carbon atoms comprising (b1) cetanol and (b2) stearyl alcohol;

(C) 0.1 mass % or more and 10 mass % or less of a surfactant comprising one or more selected from the group consisting of (c1) a nonionic surfactant selected from the group consisting of sorbitan fatty acid ester and polyoxyethylene sorbitan fatty acid ester and (c2) an anionic surfactant being fatty acid having 12 or more and 22 or less carbon atoms or a salt thereof; and (D) water, wherein the content of the ingredient (c1) is 0.05 mass % or more; a mass ratio of the content of the ingredient (A) in terms of fluorine atoms to the content of the ingredient (B), (A)/(B), is 0.001 or more and 0.2 or less; and the molar amount of (E) a polyvalent metal compound other than the ingredient (A) is less than 0.1-fold the molar amount of the ingredient (A).

[2] The oral composition according to aspect [1], wherein the content of the ingredient (A) in terms of fluorine atoms is preferably 0.01 mass % or more, more preferably 0.02 mass % or more, further preferably 0.04 mass % or more; and preferably 1 mass % or less, more preferably 0.5 mass % or less.

[3] The oral composition according to aspect [1] or [2], wherein the content of the ingredient (B) is preferably 4.5 mass % or more; and preferably 25 mass % or less, more preferably 20 mass % or less, further preferably 18 mass or less, further preferably 15 mass % or less.

[4] The oral composition according to any one of aspects [1] to [3], wherein the mass ratio of the sum of the content of the ingredient (a1) and the content of the ingredient (b2) to the content of the ingredient (B), (((b1)+(b2))/(B)), is preferably 0.85 or more, more preferably 0.9 or more, further preferably 0.92 or more; and 1 or less.

[5] The oral composition according to any one of aspects [1] to [4], wherein the mass ratio of the content of the ingredient (b1) to the content of the ingredient (b2), ((b1)/(b2)), is preferably 0.5 or more preferably 0.7 or more; and preferably 5 or less, more preferably 3 or less, further preferably 2 or less, further preferably 1.7 or less.

[6] The oral composition according to any one of aspects [1] to [5], wherein the mass ratio of the content of the ingredient (A) in terms of fluorine atoms to the content of the ingredient (B), (A)/(B), is preferably 0.002 or more, more preferably 0.003 or more; and preferably 0.1 or less, more preferably 0.05 or less.

[7] The oral composition according to any one of aspects [1] to [6], wherein a higher alcohol having 12 or more and 22 or less carbon atoms other than the ingredient (b1) and the ingredient (b2) comprises lauryl alcohol and myristyl alcohol; and the mass ratio of the sum of the content of lauryl alcohol and the content of myristyl alcohol to the content of the ingredient (B), (lauryl alcohol myristyl alcohol)/(B), is preferably 0.05 or less, more preferably 0.03 or less, further preferably 0.01 or less.

[8] The oral composition according to any one of aspects [1] to [7], wherein the content of the ingredient (C) is preferably 0.2 mass % or more, more preferably 0.3 mass % or more, further preferably 0.5 mass % or more, further preferably 1 mass % or more; and more preferably 8 mass % or less, more preferably 7 mass % or less, further preferably 6.5 mass % or less.

[9] The oral composition according to any one of aspects [1] to [8], wherein the content of the ingredient (c1) is preferably 0.2 mass % or more; and preferably 8 mass % or less, more preferably 6 mass % or less; the content when the ingredient (c2) is not contained is preferably 1 mass % or more, more preferably 1.5 mass % or more, further preferably 2 mass % or more; and the content when the ingredient (c2) is contained is preferably 0.1 mass % or more, more preferably 0.2 mass % or more, further preferably 0.4 mass % or more, more further preferably 0.5 mass % or more.

[10] The oral composition according to any one of aspects [1] to [9], wherein when the ingredient (c2) is not contained, the mass ratio of the content of the ingredient (B) to the content of the ingredient (c1), (B)/(c1), is preferably 1 or more, more preferably 1.2 or more, further preferably 1.4 or more; and preferably 10 or less, more preferably 7 or less, further preferably 5 or less, further preferably 3.5 or less.

[11] The oral composition according to any one of aspects [1] to [10], wherein the content of the ingredient (c2) in terms of fatty acids is preferably 0.05 mass % or more, more preferably 0.08 mass % or more, further preferably 0.1 mass % or more, more preferably 0.2 mass % or more, further preferably 0.4 mass % or more; and preferably 5 mass % or less, more preferably 3 mass % or less, further preferably 2.5 mass % or less, further preferably 2 mass % or less, further preferably 0.5 mass % or less, further preferably 0.2 mass % or less; or the ingredient (c2) is not contained.

[12] The oral composition according to any one of aspects [1] to [11], wherein the sum of the content of the ingredient (c1) and the content of the ingredient (c2) in terms of fatty acids is preferably 0.1 mass % or more, more preferably 0.2 mass % or more, further preferably 0.5 mass % or more, further preferably 1 mass % or more; and preferably 10 mass % or less, more preferably 8 mass % or less, further preferably 6.5 mass % or less; and both the ingredient (c1) and the ingredient (c2) are preferably contained.

[13] The oral composition according to any one of aspects [1] to [12], wherein when both the ingredient (c1) and the ingredient (c2) are contained, the mass ratio of the content of the ingredient (B) to the content of the ingredient (c1), (B)/(c1), is preferably 1 or more, more preferably 1.2 or more, further preferably 1.4 or more; and preferably 20 or less, more preferably 17 or less, further preferably 15 or less.

[14] The oral composition according to any one of aspects [1] to [13], wherein when both the ingredient (c1) and the ingredient (c2) are contained, the mass ratio of the content of the ingredient (B) to the content of the ingredient (c2), ((B)/(c2)), is preferably 2 or more, more preferably 4 or more, further preferably 5 or more; and preferably 180 or less, more preferably 150 or less, further preferably 100 or less, further preferably 90 or less.

[15] The oral composition according to any one of aspects [1] to [14], wherein the mass ratio of the content of the ingredient (B) to the sum of the content of the ingredient (c1) and the content of the ingredient (c2) in terms of fatty acids, (B)/((c1)+(c2)), is preferably higher than 1, more preferably 1.2 or more, further preferably 1.5 or more; and preferably 40 or less, more preferably 35 or less, further preferably 30 or less, further preferably 15 or less.

[16] The oral composition according to any one of aspects [1] to [15], wherein the content of a cationic surfactant other than a cationic bactericide is preferably 0.1 mass % or less, more preferably 0.05 mass % or less, further preferably 0.01 mass % or less; or the cationic surfactant other than the cationic bactericide is preferably not contained.

[17] The oral composition according to any one of aspects [1] to [16], wherein the content of the ingredient (D) is preferably 50 mass % or more, more preferably 55 mass % or more; and preferably 95 mass % or less, more preferably 92 mass % or less, further preferably 80 mass % or less.

[18] The oral composition according to any one of aspects [1] to [17], wherein the molar amount of (E) the polyvalent metal compound other than the ingredient (A) is less than 0.1-fold, preferably 0.05-fold or less, more preferably 0.01-fold or less the molar amount of the ingredient (A); or (E) the polyvalent metal compound other than the ingredient (A) is not preferably contained.

[19] The oral composition according to any one of aspects [1] to [18], wherein the content of the ingredient (E) in terms of metal atom is preferably 0.1 mass % or less, more preferably 0.01 mass % or less, further preferably 0.001 mass % or less; or the ingredient (E) is not preferably contained.

[20] The oral composition according to any one of aspects [1] to [19], wherein the content of (F) oil other than the ingredient (B), the ingredient (C), an oil-soluble medicinal ingredient, and a flavoring agent is preferably 5 mass % or less, more preferably 2 mass % or less, further preferably 1 mass % or less, further preferably 0.5 mass % or less.

[21] The oral composition according to aspect [20], wherein the mass ratio of the content of the ingredient (F) to the content of the ingredient (B), (F)/(B), is preferably less than 1, more preferably 0.5 or less, further preferably 0.3 or less.

[22] The oral composition according to any one of aspects [1] to [21], wherein the content of a cellulose binder is preferably 0.3 mass % or less, more preferably 0.25 mass % or less, further preferably 0.2 mass % or less, further preferably 0.1 mass % or less; or the cellulose binder is not preferably contained.

[23] The oral composition according to any one of aspects [1] to [22], wherein the content of the binder other than the cellulose binder in the oral composition of the present invention is preferably 0.3 mass % or less, more preferably 0.2 mass % or less, further preferably 0.1 mass % or less; or the binder other than the cellulose binder is not contained, from the viewpoint of enhancing the ability of incorporating fluoride ions into teeth.

[24] The oral composition according to any one of aspects [1] to [23], wherein the content of thickening silica is preferably 5 mass or less, more preferably 3 mass or less, further preferably 2 mass or less.

[25] The oral composition according to any one of aspects [1] to [24], wherein the content of abrasive silica is preferably 7 mass % or less, more preferably 5 mass % or less, further preferably 3 mass % or less, further preferably 2 mass or less, further preferably 1 mass or less; or the abrasive silica is not contained.

[26] The oral composition according to any one of aspects [1] to [25], wherein the content of a sugar alcohol is preferably 30 mass % or less, more preferably 20 mass % or less, further preferably 15 mass or less; and preferably 1 mass % or more, more preferably 2 mass % or more, further preferably 5 mass % or more.

[27] The oral composition according to any one of aspects [1] to [26], wherein the total content of a water-absorbing ingredient being solid at 20° C. and selected from the group consisting of abrasive silica, sorbitol, and xylitol is preferably 35 mass % or less, more preferably 30 mass % or less, further preferably 25 mass % or less, further preferably 20 mass % or less.

[28] The oral composition according to any one of aspects [1] to [27], wherein the composition has a viscosity at 20° C. of preferably 5,000 dPa·s or less, more preferably 4,000 dPa·s or less, further preferably 3,800 dPa·s or less; and preferably 300 dPa·s or more, more preferably 400 dPa·s or more, further preferably 500 dPa·s or more, further preferably 700 dPa·s or more.

[29] A method of producing the oral composition according to any one of aspects [1] to [28], comprising:
a step (I) of mixing a mixture liquid comprising the ingredient (B) and the ingredient (C) at a temperature not lower than the melting point of the ingredient (B) and not higher than 90° C., more preferably at a temperature not lower than the melting point of the ingredient (B) and not higher than 85° C., further preferably at a temperature not lower than 80° C. and not higher than 85° C., and
a step (II) of adding thereto the ingredient (A).

[30] The oral composition according to any one of aspects [1] to [28], wherein the composition is an agent for promoting incorporation of fluoride ions into teeth.

[31] Use of the oral composition according to any one of aspects [1] to [28] for promoting incorporation of fluoride ions into teeth.

[32] Use of the oral composition according to any one of aspects [1] to [28] for producing an agent for promoting incorporation of fluoride ions into teeth.

[33] A method for incorporating fluoride ions into teeth by applying the oral composition according to any one of aspects [1] to [28] into the oral cavity and, after the application, preferably rinsing the oral cavity with water.

EXAMPLES

The present invention will now be specifically described based on Examples. The content of each ingredient is represented by mass % unless otherwise specified in the Table.

Examples 1 to 18 and Comparative Examples 1 to 3

Each oral composition was produced according to the prescriptions shown in Tables 1 and 2. Specifically, the ingredient (B), and the ingredient (C) were heated to 80° C. (80° C. to 82° C.), mixed, followed by stirring for about 10 minutes. Subsequently, the ingredient (D) was added to and mixed with the mixture. The ingredient (A) and other ingredients were then added to and mixed for 10 minutes with the resulting mixture to give an oral composition.

Each of the resulting oral compositions was subjected to measurement of the viscosity and the amount of incorporated fluoride ions according to the following methods, and the formation of α-gel was investigated.

The results are shown in Tables 1 and 2.

<<Investigation of α-Gel Formation>>

Each of the resulting oral compositions was investigated whether α-gel was formed or not by wide angle X-ray diffraction. Specifically, formation of α-gel was determined by whether one sharp diffraction peak appeared at a Bragg angle of about 21° to 22° or not in wide angle X-ray diffraction.

Specifically, as also shown in FIG. 1, when one sharp diffraction peak was observed at a Bragg angle of about 21° to 23° and it was confirmed that the composition had an α-gel structure formed, the composition was evaluated as "Existed", and when such a peak was not observed, the composition was evaluated as "Not existed". FIG. 1 shows the diffraction X-ray intensity distribution in wide angle X-ray diffraction of the α-gel formed in the composition of Example 1.

<<Measurement of Amount of Incorporated Fluoride Ions>>

Each of the resulting oral compositions was diluted with ion-exchanged water by four times to prepare the respective aqueous solutions. A HAP pellet (APP-100, HOYA Corporation) of 10 mm×10 mm×2 mm was immersed in each aqueous solution for 3 minutes, was then washed with ion-exchanged water to remove the oral composition, and was dried at room temperature (25° C.). Fluoride ions were extracted for 30 seconds from the dried pellet by addition of 1 mL of 1 N hydrochloric acid. Subsequently, 2 mL of 3 M trisodium citrate and 1 mL of ion-exchanged water were added to the extract, and then 4 mL of buffer TSABII (Thermo Scientific) was added thereto to prepare a solution for quantitative analysis of fluoride ions. This solution was used as a measurement sample, and the amount of fluoride adsorbed on the HAP pellet was measured with an ion analyzer (Expandable ion Analyzer EA 940 (manufactured by ORION)) using a fluoride ion electrode (ion plus 20 Fluoride (manufactured by ORION)) and was regarded as the incorporation amount of fluoride ions. In the HAP pellet used, the sides were covered with manicure, and the upper and lower surfaces were mirror polished using a waterproof abrasive paper until the surfaces were smoothened.

TABLE 1

| | | Example 1 | Example 2 | Example 3 | Example 4 | Example 5 | Example 6 | Example 7 |
|---|---|---|---|---|---|---|---|---|
| (A) | Sodium fluoride | 0.21 | 0.21 | 0.21 | 0.21 | 0.21 | 0.21 | 0.32 |
| (B) | Cetanol (b1) | 2.11 | 4.22 | 4.22 | 5.10 | 3.15 | 3.15 | 4.22 |
| | Stearyl alcohol (b2) | 2.65 | 5.30 | 5.30 | 6.40 | 4.00 | 4.00 | 5.30 |
| | Lauryl alcohol | 0.08 | 0.15 | 0.15 | 0.18 | 0.11 | 0.11 | 0.15 |
| | Myristyl alcohol | 0.16 | 0.33 | 0.33 | 0.32 | 0.24 | 0.24 | 0.33 |
| (C) | Polyoxyethylene sorbitan monostearate*[1](c1) | 2.5 | 5.0 | 0.5 | 6.0 | | | 5.0 |
| | Sorbitan monooleate*[2](c1) | | | | | 4.5 | | |
| | Sorbitan monostearate A*[3](c1) | | | 1.0 | | | 5.0 | |
| | Sorbitan monostearate B*[4](c1) | | | | | | | |
| | Stearic acid (c2) | | | 0.5 | | | | |
| | Palmitic acid (c2) | | | | | | | |
| | Potassium hydroxide (48%) | | | 0.1 | | | | |
| | Polyoxyethylene hydrogenated castor oil | | | | | | | |
| | Vaseline | | | | | | | |
| | Sorbitol liquid (70%) | 20 | 20 | 20 | 20 | 20 | 20 | 20 |
| | Flavoring agent | 1 | 1 | 1 | 1 | 1 | 1 | 1 |
| | Purified water | 71.29 | 63.79 | 66.69 | 60.79 | 66.79 | 66.29 | 63.68 |
| | Total | 100.00 | 100.00 | 100.00 | 100.00 | 100.00 | 100.00 | 100.00 |
| (D) | Water amount | 77.29 | 69.79 | 72.74 | 66.79 | 72.79 | 72.29 | 69.68 |
| | Amount of ingredient (A) in terms of fluorine atoms | 0.095 | 0.095 | 0.095 | 0.095 | 0.095 | 0.095 | 0.144 |
| | (A)/(B) | 0.020 | 0.010 | 0.010 | 0.008 | 0.013 | 0.013 | 0.015 |
| | (B) | 5 | 10 | 10 | 12 | 8 | 8 | 10 |
| | (B)/(c1) | 2.0 | 2.0 | 6.7 | 2.0 | 1.7 | 1.5 | 2.0 |
| | (B)/(c2) | — | — | 20 | — | — | — | — |
| | (B)/((c1) + (c2)) | 2.0 | 2.0 | 5.0 | 2.0 | 1.7 | 1.5 | 2.0 |
| Formation of α-gel | | Existed | Existed | Existed | Existed | Existed | Existed | Existed |
| Amount of incorporated fluoride ions (ppm) | | 0.309 | 0.516 | 1.435 | 2.240 | 0.401 | 0.388 | 0.780 |

| | | Example 8 | Example 9 | Example 10 | Comparative Example 1 | Comparative Example 2 | Comparative Example 3 |
|---|---|---|---|---|---|---|---|
| (A) | Sodium fluoride | 0.21 | 0.1 | 0.32 | 0.21 | 0.21 | 0.21 |
| (B) | Cetanol (b1) | 4.22 | 5.10 | 2.11 | 1.41 | 3.15 | |
| | Stearyl alcohol (b2) | 5.30 | 6.40 | 2.65 | 1.43 | 4.00 | 4.00 |
| | Lauryl alcohol | 0.15 | 0.18 | 0.08 | 0.05 | 0.11 | |
| | Myristyl alcohol | 0.33 | 0.32 | 0.16 | 0.11 | 0.24 | |
| (C) | Polyoxyethylene sorbitan monostearate*[1](c1) | 0.5 | 6.0 | 2.5 | 2.5 | | |
| | Sorbitan monooleate*[2](c1) | | | | | | |
| | Sorbitan monostearate A*[3](c1) | 1.0 | | | | | |
| | Sorbitan monostearate B*[4](c1) | | | | | | 5.0 |
| | Stearic acid (c2) | | | | | | |
| | Palmitic acid (c2) | 0.5 | | | | | |
| | Potassium hydroxide (48%) | 0.1 | | | | | |
| | Polyoxyethylene hydrogenated castor oil | | | | | 2.5 | |
| | Vaseline | | | | | | 3.5 |
| | Sorbitol liquid (70%) | 20 | 20 | 20 | 20 | 20 | 20 |
| | Flavoring agent | 1 | 1 | 1 | 1 | 1 | 1 |
| | Purified water | 66.69 | 60.9 | 71.18 | 73.29 | 68.79 | 66.29 |
| | Total | 100.00 | 100.00 | 100.00 | 100.00 | 100.00 | 100.00 |
| (D) | Water amount | 72.74 | 66.90 | 77.18 | 79.29 | 74.79 | 72.29 |
| | Amount of ingredient (A) in terms of fluorine atoms | 0.095 | 0.045 | 0.144 | 0.095 | 0.095 | 0.095 |

TABLE 1-continued

| | | | | | | |
|---|---|---|---|---|---|---|
| (A)/(B) | 0.010 | 0.004 | 0.030 | 0.033 | 0.013 | 0.024 |
| (B) | 10 | 12 | 5 | 3 | 8 | 4 |
| (B)/(c1) | — | 2.0 | 2.0 | 1.2 | — | — |
| (B)/(c2) | 20 | — | — | — | — | — |
| (B)/(c1) + (c2)) | 5.0 | 2.0 | 2.0 | 1.2 | — | 0.8 |
| Formation of α-gel | Existed | Existed | Existed | Not existed | Not existed | Not existed |
| Amount of Incorporated fluoride ions (ppm) | 1.356 | 1.084 | 0.487 | 0.046 | 0.031 | 0.025 |

[1] Rheodol TW-S120V, manufactured by Kao Corporation
[2] Rheodol AO-10V, manufactured by Kao Corporation
[3] Rheodol AS-10V, manufactured by Kao Corporation
[4] Rheodol SP-S10V, manufactured by Kao Corporation (changed from [3] for dispersing Vaseline)

TABLE 2

| | Example 11 | Example 12 | Example 13 | Example 14 | Example 15 | Example 16 | Example 17 | Example 18 |
|---|---|---|---|---|---|---|---|---|
| (A) Sodium fluoride | 0.11 | 0.11 | 0.11 | 0.15 | | 0.21 | 0.21 | 0.21 |
| Ammonium fluoride | 0.09 | | | | | | | |
| Potassium fluoride | | 0.14 | | | | | | |
| Tin fluoride | | | 0.37 | 0.25 | | | | |
| Sodium monofluorophosphate | | | | | 0.72 | | | |
| (B) Cetanol (b1) | 5.1 | 5.1 | 5.1 | 5.1 | 5.1 | 4.22 | 4.22 | 7.4 |
| Stearyl alcohol (b2) | 6.4 | 6.4 | 6.4 | 6.4 | 6.4 | 5.3 | 5.3 | 9.3 |
| Lauryl alcohol | 0.18 | 0.18 | 0.18 | 0.18 | 0.18 | 0.15 | 0.15 | 0.26 |
| Myristyl alcohol | 0.32 | 0.32 | 0.32 | 0.32 | 0.32 | 0.33 | 0.33 | 0.56 |
| (C) Polyoxyethylene sorbitan monostearate[1](c1) | | | | | | 0.5 | 0.5 | 5.0 |
| Polyoxyethylene sorbitan monooleate[5](c1) | 6.0 | 6.0 | 6.0 | 6.0 | 6.0 | | | |
| Sorbitan monooleate[2](c1) | | | | | | | | 3.5 |
| Sorbitan monostearate A[3](c1) | | | | | | | | |
| Sorbitan monostearate B[4](c1) | | | | | | | | |
| Stearic acid (c2) | | | | | | 2.0 | 0.5 | |
| Palmitic acid (c2) | | | | | | | | |
| Potassium hydroxide (48%) | | | | | | 0.50 | 0.05 | |
| Polyoxyethylene hydrogenated castor oil | | | | | | | | |
| Vaseline | | | | | | | | |
| Sorbitol liquid (70%) | 20 | 20 | 20 | 20 | 20 | 20 | 20 | 20 |
| Flavoring agent | 1 | 1 | 1 | 1 | 1 | 1 | 1 | 1 |
| Purified water | 60.8 | 60.75 | 60.52 | 60.6 | 60.28 | 65.79 | 67.74 | 52.77 |
| Total | 100.00 | 100.00 | 100.00 | 100.00 | 100.00 | 100.00 | 100.00 | 100.00 |
| (D) Water amount | 66.80 | 66.75 | 66.52 | 66.60 | 66.28 | 72.05 | 73.77 | 58.77 |
| Amount of ingredient (A) in terms of fluorine atoms | 0.096 | 0.096 | 0.095 | 0.098 | 0.095 | 0.095 | 0.095 | 0.095 |
| (A)/(B) | 0.008 | 0.008 | 0.008 | 0.008 | 0.008 | 0.009 | 0.009 | 0.005 |
| (B) | 12 | 12 | 12 | 12 | 12 | 10 | 10 | 18 |
| (B)/(c1) | 2.0 | 2.0 | 2.0 | 2.0 | 2.0 | 20.0 | 20.0 | 2.1 |
| (B)/(c2) | — | — | — | — | — | 5 | 20 | — |
| (B)/((c1) + (c2)) | 2.0 | 2.0 | 2.0 | 2.0 | 2.0 | 4.0 | 10.0 | 2.1 |
| Formation of α-gel | Existed | Existed | Existed | Existed | Existed | Existed | Existed | Existed |
| Amount of incorporated fluoride ions (ppm) | 0.098 | 0.156 | 0.191 | 0.320 | 0.076 | 0.094 | 0.084 | 0.085 |

[1-4] The same as those in Table 1
[5] Rheodol TW-O120V, manufactured by Kao Corporation As a result of Table 1 and Table 2, the dentifrice of each Example effectively forms α-gel and effectively increases the ability of incorporating fluoride ions into teeth.

What is claimed is:

1. An oral composition comprising the following ingredients (A), (B), (C), and (D):
(A) 0.005 mass % or more and 2 mass % or less, in terms of fluorine atoms, of one or more fluoride ion-supplying compounds selected from the group consisting of sodium fluoride, ammonium fluoride, potassium fluoride, sodium monofluorophosphate, and tin fluoride;
(B) 4 mass % or more and 30 mass % or less of a higher alcohol having 12 or more and 22 or less carbon atoms comprising (b1) cetanol and (b2) stearyl alcohol;
(C) 0.1 mass % or more and 10 mass % or less of a surfactant comprising one or more selected from the group consisting of (c1) a nonionic surfactant selected from the group consisting of sorbitan fatty acid ester and polyoxyethylene sorbitan fatty acid ester and (c2) an anionic surfactant being fatty acid having 12 or more and 22 or less carbon atoms or a salt thereof; and
(D) water,
wherein the content of the ingredient (c1) is 0.05 mass % or more; a mass ratio of the content of the ingredient (A) in terms of fluorine atoms to the content of the ingredient (B), (A)/(B), is 0.001 or more and 0.2 or less; and the molar amount of (E) a polyvalent metal compound other than the ingredient (A) is less than 0.1-fold the molar amount of the ingredient (A).

2. The oral composition according to claim 1, wherein
when the ingredient (C) does not contain the ingredient (c2), a mass ratio of the content of the ingredient (B) to the content of the ingredient (c1), (B)/(c1), is 1 or more and 10 or less; and
when the ingredient (C) contains both the ingredient (c1) and the ingredient (c2), a mass ratio of the content of the ingredient (B) to the content of the ingredient (c1), (B)/(c1), is 1 or more and 10 or less; and a mass ratio of the content of the ingredient (B) to the content of the ingredient (c2), (B)/(c2), is 2 or more and 180 or less.

3. The oral composition according to claim 1, wherein a mass ratio of the content of the ingredient (b1) to the content of the ingredient (b2), ((b1)/(b2)), is 0.5 or more and 5 or less.

4. The oral composition according to claim 1, wherein a mass ratio of the sum of the content of the ingredient (b1) and the content of the ingredient (b2) to the content of the ingredient (B), (((b1)+(b2))/(B)), is 0.85 or more and 1 or less.

5. The oral composition according to claim 1, wherein the content of a cellulose binder is 0.3 mass % or less.

6. The oral composition according to claim 5, wherein the cellulose binder is one or two selected from the group consisting of sodium carboxymethyl cellulose and hydroxyalkyl cellulose.

7. The oral composition according to claim 1, wherein the content of a water-absorbing ingredient being solid at 20° C. and selected from the group consisting of abrasive silica, sorbitol, and xylitol is 30 mass % or less.

8. The oral composition according to claim 1, wherein a mass ratio of the content of the ingredient (B) to the sum of the content of the ingredient (c1) and the content of the ingredient (c2) in terms of fatty acids, (B)/((c1)+(c2)), is higher than 1 and 40 or less.

9. The oral composition according to claim 1, wherein a mass ratio of the content of (F) oil other than the ingredient (B), the ingredient (C), an oil-soluble medicinal ingredient, and a flavoring agent to the content of the ingredient (B), (F)/(B), is less than 1.

10. The oral composition according to claim 1, wherein the content of the ingredient (D) is 50 mass % or more and 95 mass % or less.

11. The oral composition according to claim 1, wherein the content of polyoxyethylene hydrogenated castor oil is 0.5 mass % or less.

12. The oral composition according to claim 1, wherein the composition is an agent for promoting incorporation of fluoride ions into teeth.

13. A method of producing the oral composition according to claim 1, comprising:

a step (I) of mixing a mixture liquid comprising the ingredient (B) and the ingredient (C) at a temperature not lower than the melting point of the ingredient (B) and not higher than 90° C.; and
a step (II) of adding thereto the ingredient (A).

14. A method for incorporating fluoride ions into teeth by applying the composition according to claim 1 into the oral cavity.

15. An oral composition comprising the following ingredients (A), (B), (C), and (D):
(A) 0.005 mass % or more and 2 mass % or less, in terms of fluorine atoms, of one or more fluoride ion-supplying compounds selected from the group consisting of sodium fluoride, ammonium fluoride, potassium fluoride, sodium monofluorophosphate, and tin fluoride;
(B) 4 mass % or more and 30 mass % or less of a higher alcohol having 12 or more and 22 or less carbon atoms comprising (b1) cetanol and (b2) stearyl alcohol;
(C) 0.1 mass % or more and 10 mass % or less of a surfactant comprising one or more selected from the group consisting of (c1) a nonionic surfactant selected from the group consisting of sorbitan fatty acid ester and polyoxyethylene sorbitan fatty acid ester and (c2) an anionic surfactant being fatty acid having 12 or more and 22 or less carbon atoms or a salt thereof; and
(D) water,
wherein:
the content of the ingredient (c1) is 0.05 mass % or more;
a mass ratio of the content of the ingredient (A) in terms of fluorine atoms to the content of the ingredient (B), (A)/(B), is 0.001 or more and 0.2 or less;
the molar amount of (E) a polyvalent metal compound other than the ingredient (A) is less than 0.1-fold the molar amount of the ingredient (A);
wherein,
when the ingredient (C) does not contain the ingredient (c2), a mass ratio of the content of the ingredient (B) to the content of the ingredient (c1), (B)/(c1), is 1 or more and 10 or less;
when the ingredient (C) contains both the ingredient (c1) and the ingredient (c2), a mass ratio of the content of the ingredient (B) to the content of the ingredient (c1), (B)/(c1), is 1 or more and 10 or less and a mass ratio of the content of the ingredient (B) to the content of the ingredient (c2), (B)/(c2), is 2 or more and 180 or less.

16. The oral composition of claim 1, wherein the content of the ingredient (c1) is 0.05 mass % or more and 10 mass % or less.

17. The oral composition of claim 15, wherein the content of the ingredient (c1) is 0.05 mass % or more and 10 mass % or less.

* * * * *